United States Patent
Baba et al.

(10) Patent No.: US 8,512,304 B2
(45) Date of Patent: Aug. 20, 2013

(54) ABSORBENT ARTICLE AND METHOD FOR MAKING THE SAME

(75) Inventors: Toshimitsu Baba, Kanonji (JP); Takanori Matsuo, Kanonji (JP); Hiroyuko Soga, Kanonji (JP); Junichi Noguchi, Kanonji (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 489 days.

(21) Appl. No.: 11/964,451

(22) Filed: Dec. 26, 2007

(65) Prior Publication Data

US 2008/0161768 A1    Jul. 3, 2008

(30) Foreign Application Priority Data

Dec. 27, 2006  (JP) ................................. 2006-353261

(51) Int. Cl.
*A61F 13/15* (2006.01)
(52) U.S. Cl.
USPC .................................................... 604/385.27
(58) Field of Classification Search
USPC .............. 604/385.22–385.31, 385.24–385.27
See application file for complete search history.

(56) References Cited

U.S. PATENT DOCUMENTS

| | | | | |
|---|---|---|---|---|
| 5,055,103 A | * | 10/1991 | Nomura et al. | 604/385.29 |
| 5,147,487 A | * | 9/1992 | Nomura et al. | 156/164 |
| 5,342,341 A | * | 8/1994 | Igaue et al. | 604/385.29 |
| 5,447,508 A | * | 9/1995 | Numano et al. | 604/385.27 |
| 5,569,232 A | * | 10/1996 | Roe et al. | 604/385.3 |
| 5,749,865 A | * | 5/1998 | Yamamoto et al. | 604/385.29 |
| 5,916,206 A | * | 6/1999 | Otsubo et al. | 604/385.27 |
| 6,179,820 B1 | * | 1/2001 | Fernfors | 604/385.27 |
| 6,482,196 B1 | * | 11/2002 | Hisada | 604/385.3 |
| 6,595,976 B2 | * | 7/2003 | Jitoe et al. | 604/385.29 |
| 6,602,238 B2 | * | 8/2003 | Takei et al. | 604/385.26 |
| 6,726,669 B2 | * | 4/2004 | Shimada et al. | 604/385.29 |
| 7,331,946 B2 | * | 2/2008 | Shimada et al. | 604/385.3 |
| 2003/0139726 A1 | * | 7/2003 | Gibbs | 604/385.29 |
| 2004/0013850 A1 | * | 1/2004 | Kling | 428/98 |
| 2004/0167494 A1 | * | 8/2004 | Otsubo | 604/385.27 |
| 2005/0090790 A1 | * | 4/2005 | Veith | 604/385.01 |
| 2005/0096624 A1 | * | 5/2005 | Hoshino et al. | 604/385.27 |
| 2005/0131365 A1 | * | 6/2005 | Sakaguchi | 604/367 |
| 2005/0137563 A1 | * | 6/2005 | Van Gompel et al. | 604/385.27 |
| 2005/0215963 A1 | * | 9/2005 | Autran et al. | 604/358 |
| 2006/0032578 A1 | * | 2/2006 | Schneider | 156/160 |
| 2006/0111686 A1 | * | 5/2006 | Schneider | 604/385.26 |

(Continued)

FOREIGN PATENT DOCUMENTS

EP        1155668 A2 * 11/2001
JP        08-071103        3/1996

(Continued)

*Primary Examiner* — Melanie Hand
(74) *Attorney, Agent, or Firm* — Morrison & Foerster LLP

(57) ABSTRACT

An absorbent article includes a chassis, an absorbent structure placed on the chassis and elastic elements attached under tension to the chassis so as to extend across an absorbent structure region of the chassis occupied by the absorbent structure and to extend outward beyond opposite side edges of the absorbent structure. An elongation percentage of the elastic elements 6 is relatively low in the absorbent structure region as well as in first side regions outside opposite side edges of the absorbent structure and the elongation percentage is relatively high in second side regions outside the first side region and gradually increases as the elastic elements draw away from the first side regions toward the second side regions.

3 Claims, 6 Drawing Sheets

(56) References Cited

U.S. PATENT DOCUMENTS

| | | | |
|---|---|---|---|
| 2006/0129119 A1* | 6/2006 | Kistler | 604/385.14 |
| 2007/0208316 A1* | 9/2007 | Nakahata et al. | 604/385.02 |
| 2007/0208317 A1* | 9/2007 | Krautkramer et al. | 604/385.3 |
| 2007/0287975 A1* | 12/2007 | Fujimoto et al. | 604/385.3 |
| 2008/0027406 A1* | 1/2008 | Shirai et al. | 604/385.24 |
| 2008/0058750 A1* | 3/2008 | Erdman et al. | 604/385.3 |
| 2008/0082073 A1* | 4/2008 | Driskell et al. | 604/385.22 |
| 2009/0143756 A1* | 6/2009 | Hornung et al. | 604/385.23 |

FOREIGN PATENT DOCUMENTS

| | | |
|---|---|---|
| JP | 2002320641 | 11/2002 |
| JP | 2006043125 | 2/2006 |
| WO | WO 2004006817 A1 * | 1/2004 |

* cited by examiner

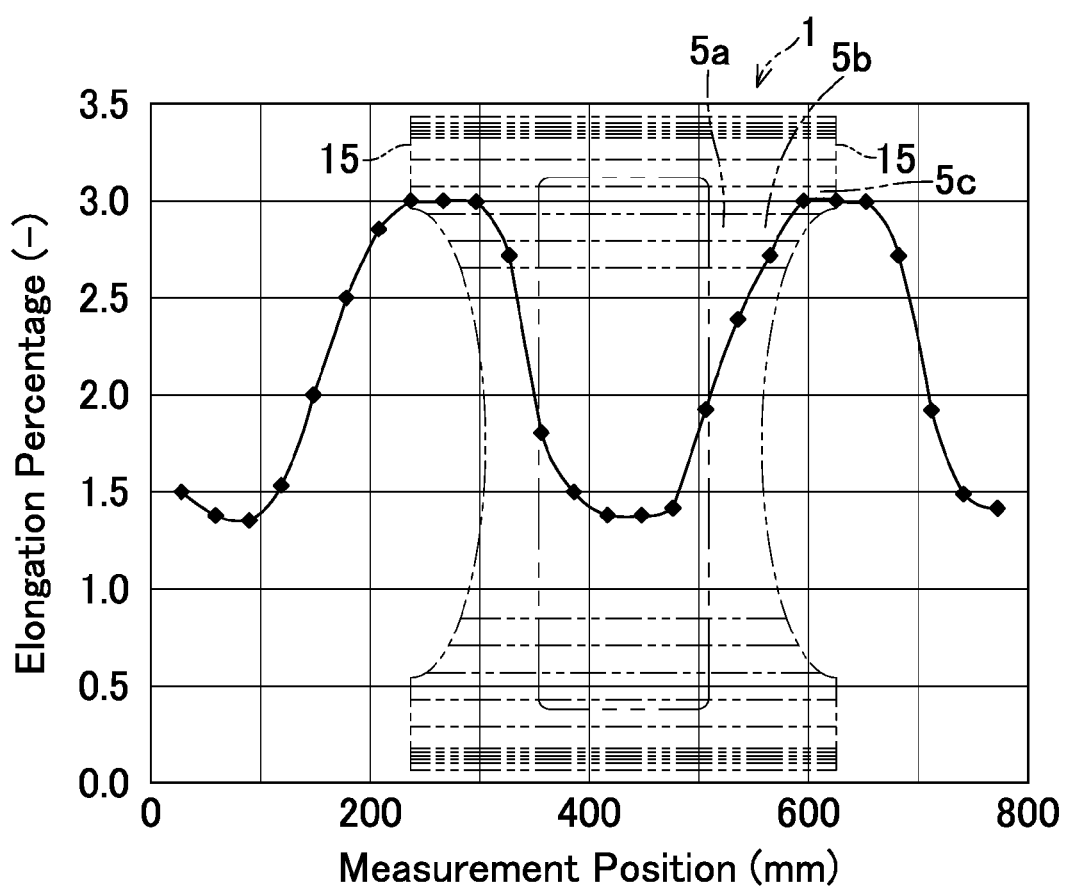

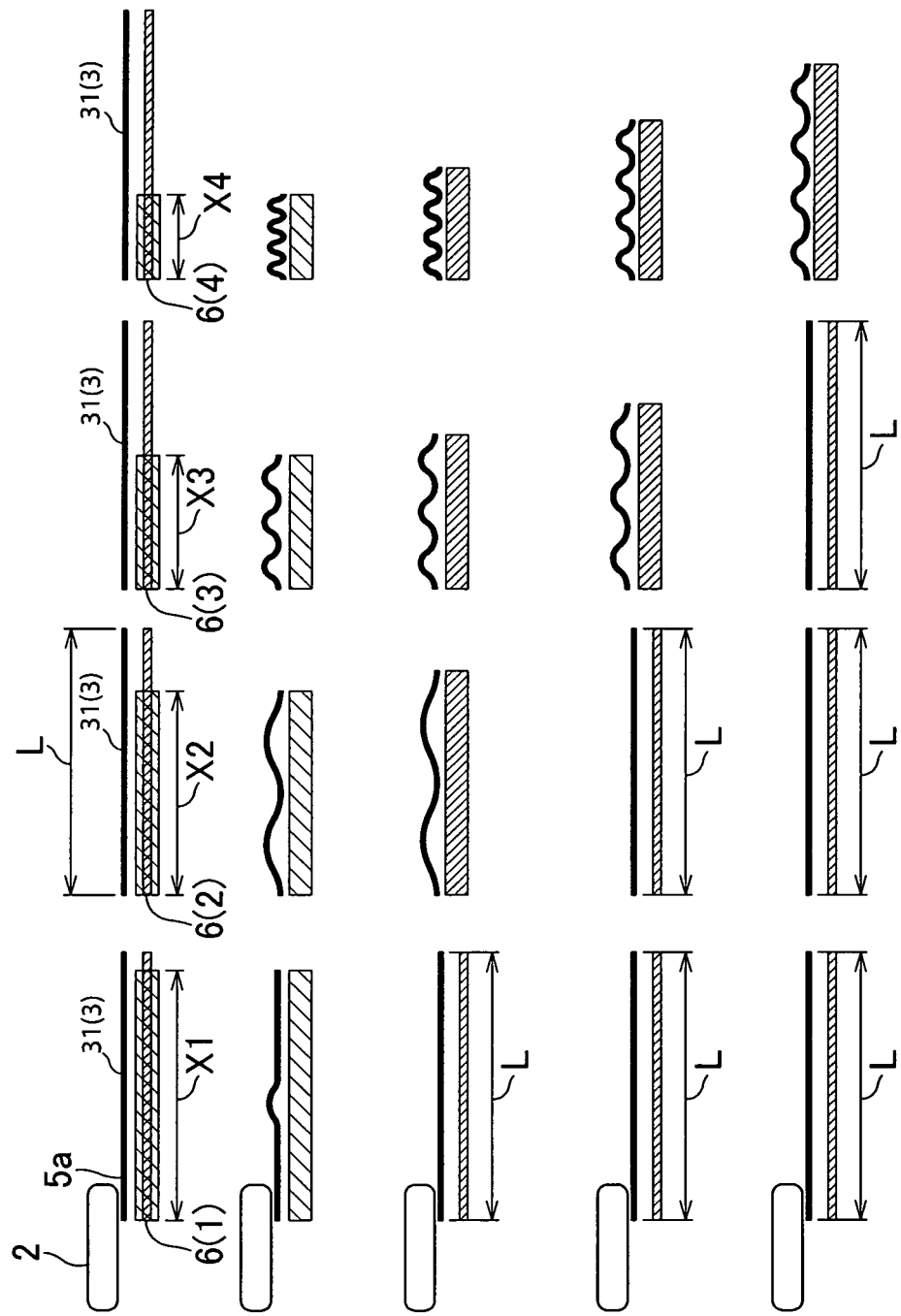

ABSORBENT ARTICLE AND METHOD FOR MAKING THE SAME

CROSS REFERENCE TO RELATED APPLICATIONS

This application claims the benefit under 35 5 U.S.C. §119 of Japanese Patent Application 2006-353261 filed on Dec. 27, 2006, the contents of which are hereby incorporated by reference in their entirety.

BACKGROUND OF THE INVENTION

This invention relates generally to an absorbent article and a method for making the same.

Absorbent articles comprising a chassis and an absorbent structure attached thereto have been extensively used in the form of disposable diapers, sanitary napkins, etc. In order to improve a fit of such absorbent article to its wearer's body, it is well known to provide the chassis with elastic elements extending across a region occupied by the absorbent structure.

For example, Japanese Unexamined Patent Application Publication No. 1996-71103 discloses a disposable diaper comprising a topsheet, a backsheet and an absorbent structure sandwiched between these sheets, waist elastic elements extending along waist bands and auxiliary elastic elements extending in a waist circling direction between the waist elastic elements and leg elastic elements, wherein the auxiliary elastic elements extend at least partially across a region occupied by the absorbent structure and a total elasticity measured in a region occupied by the absorbent structure and the auxiliary elastic elements is defined by an elongation percentage less than 25% before the diaper is put on the wearer's body and an elongation percentage of 25% or higher during use of the diaper while the independent elasticity of the absorbent structure itself is defined by an elasticity modulus in a range of $1.0 \times 10^3$ to $2.5 \times 10^5$ g/cm$^2$ and a flexural rigidity in a range of 20 to 200 g/cm.

In the case of the diaper disclosed in Japanese Unexamined Patent Application Publication No. 1996-71103, the auxiliary elastic elements may be prevented by the absorbent structure against excessive contraction because the auxiliary elastic elements extend at least partially across the region occupied by the absorbent structure. In addition, the diaper may be deformed depending on a body shape of the individual wearer and thereby a fit of the diaper to the wearer's body may be improved.

However, with the construction of prior art, for example, as disclosed in Japanese Unexamined Patent Application Publication No. 1996-71103 such that the auxiliary elastic elements extend across the region occupied by the absorbent structure, it is inevitable that the absorbent structure is pulled by the auxiliary elastic elements as these elastic elements contract. For example, the absorbent structure may move out of its proper position in the vicinity of the central zone of a crotch region of the diaper as a force is exerted on the auxiliary elastic elements due to the movement of the wearer's body. Such displacement of the absorbent structure may result in deterioration of a feeling to wear the diaper and/or the desired function of the absorbent article.

SUMMARY OF THE INVENTION

In view of the problem as has been described above, it is an object of the this invention to provide an absorbent article improved so that a good fit to the wearer's body is assured and displacement of the absorbent structure is restrained. It is also an object of this invention to provide a method for making such an absorbent article.

A first aspect of this invention pertains to an absorbent article, comprising: a chassis having a front waist region, a rear waist region, a crotch region, a front waist band associated with the front waist region and a rear waist band associated with the rear waist region and being substantially non-stretchable and liquid-impermeable in at least the crotch region. The absorbent article may also comprise an absorbent structure extending from the crotch region into the front and rear waist region. The absorbent article may also comprise first elastic elements extending outside of opposite side edges of the absorbent structure and crossing an absorbent structure occupied by the absorbent structure in a cross-body direction. According to the invention, an elongation percentage of the first elastic elements is lower in the absorbent structure region as well as in first side regions adjacent to opposite side edges of the absorbent structure region and is higher in second side regions adjacent to outsides of the first side regions, and the elongation percentage gradually increases from each first side region toward each second side region.

A second aspect of this invention pertains to an absorbent article, comprising: a chassis having a front waist region, a rear waist region, a crotch region, a front waist band associated with the front waist region and a rear waist band associated with the rear waist region and being substantially non-stretchable and liquid-impermeable in at least the crotch region. According to the second aspect, the absorbent article also has an absorbent structure extending from the crotch region into the front and rear waist region. According to the second aspect, the absorbent article has first elastic elements extending outside of opposite side edges of the absorbent structure and crossing an absorbent structure occupied by the absorbent structure in a cross-body direction. An elongation percentage of the first elastic elements is lower in the absorbent structure region as well as in first side regions adjacent to opposite side edges of the absorbent structure region and is higher in second side regions adjacent to outsides of the first side regions, and the elongation percentage gradually increases from each first side region toward each second side region while the elongation percentage is substantially constant in a vicinity region of each of opposite side edges of the chassis in each of the second side regions.

A third aspect of this invention pertains to a method for making an absorbent article according to one of the foregoing first and second aspects, the method comprises the steps of; continuously feeding the chassis at a constant feed rate; continuously feeding the first elastic elements in the same direction as the direction in which the chassis is fed at feed rate periodically changing according to a predetermined rule so that the elongation percentage periodically change and bonding the first elastic elements to the chassis; and bonding the absorbent structure to the absorbent structure region in which the periodically changing elongation percentage is relatively low.

The term "substantially non-stretchable" as used herein means that the absorbent article is substantially not deformed even if a force is exerted thereon during usual use of the article. The term "elongation percentage" as used herein refers to a value corresponds to a fraction of stretched length of the elastic elements under a load/length thereof under no load. It should be noted that the expression as used herein "the elongation percentage of the elastic elements continuously changes" includes two cases. In one of these two cases, the elastic elements having an elongation percentage continuously changing is intermittently bonded to the chassis so that the elongation percentage changes in multistage. The other case, the elastic elements having an elongation percentage continuously changing is continuously bonded to the chassis so that the elongation element smoothly changes.

The first and second aspects of this invention include the following preferred embodiments.

The article further comprises second elastic elements, a tensile stress of the first elastic elements is lower than that of the second elastic elements.

The first elastic elements are intermittently secured to the chassis.

The first elastic elements are secured to the chassis except in the absorbent structure region.

The third aspect of this invention includes the following preferred embodiments.

The elongation percentage of the first elastic elements is periodically changed in fashion of monotonic increase and monotonic decrease.

The elongation percentage of the first elastic elements is maintained constant in the second side regions in a relative high domain of the periodically changing elongation percentage.

The first elastic elements are not bonded to the chassis in the absorbent structure region.

The first elastic elements are intermittently bonded to the chassis.

In the absorbent article according to this invention, the first elastic elements are attached under tension to the chassis so as to extend across the first and second side regions of the absorbent structure region occupied by the absorbent structure and to extend linearly outward further beyond the side edges of the absorbent structure. The first elastic elements ensure a good fit of the absorbent structure to the ventral side and the dorsal side of the wearer.

The first elastic elements are intermittently bonded to the first and second side regions of the non-stretchable chassis so that the elongation percentage of the first elastic elements are relatively low in the absorbent structure region and the first side regions of the chassis. The elongation percentage of the first elastic elements continuously changes within a range of relatively high levels as the distance from the first side regions toward the second side regions increases.

As will be described later in more detail, such arrangement ensures that a displacement of the first side regions of the absorbent structure is negligible even if any force tending to stretch the first elastic elements is exerted on these regions. The elongation percentage of the first elastic elements may be gradually increased as the distance from the first side regions of the absorbent structure and the vicinity thereof increases to avoid undesirable displacement of the absorbent structure.

According to the method according to this invention, the absorbent article including the first elastic elements of which the elongation percentage continuously changes can be continuously made without any apprehension that the production rate might decrease and the production equipment might be complexified.

BRIEF DESCRIPTION OF THE DRAWINGS

FIG. 5 is a graphic diagram exemplarily showing a pattern in which elongation percentage of the first elastic elements are distributed;
and
FIGS. 6A-6E are schematic diagrams illustrating the behavior of the first elastic elements, wherein
FIG. 6A illustrates the first elastic elements immediately after attached under tension,
FIG. 6B illustrates the first elastic elements left free to contract, and FIGS. 6C, D and E respectively illustrate the first elastic elements stretched progressively from the state illustrated in FIG. 6B.

DETAILED DESCRIPTION OF THE PREFERRED EMBODIMENTS

Details of an absorbent article according to this invention will be more fully understood from the description given hereunder on the basis of a disposable diaper as a typical embodiment of the invention. Of the accompanying drawings, FIG. 1 is an exploded perspective view of the diaper 1 and FIG. 2 is a plan view with a partial cutaway showing the diaper 1 developed and flattened as viewed from the side of an outer covering, i.e., the side facing away from the diaper wearer's skin.

Figure 1:
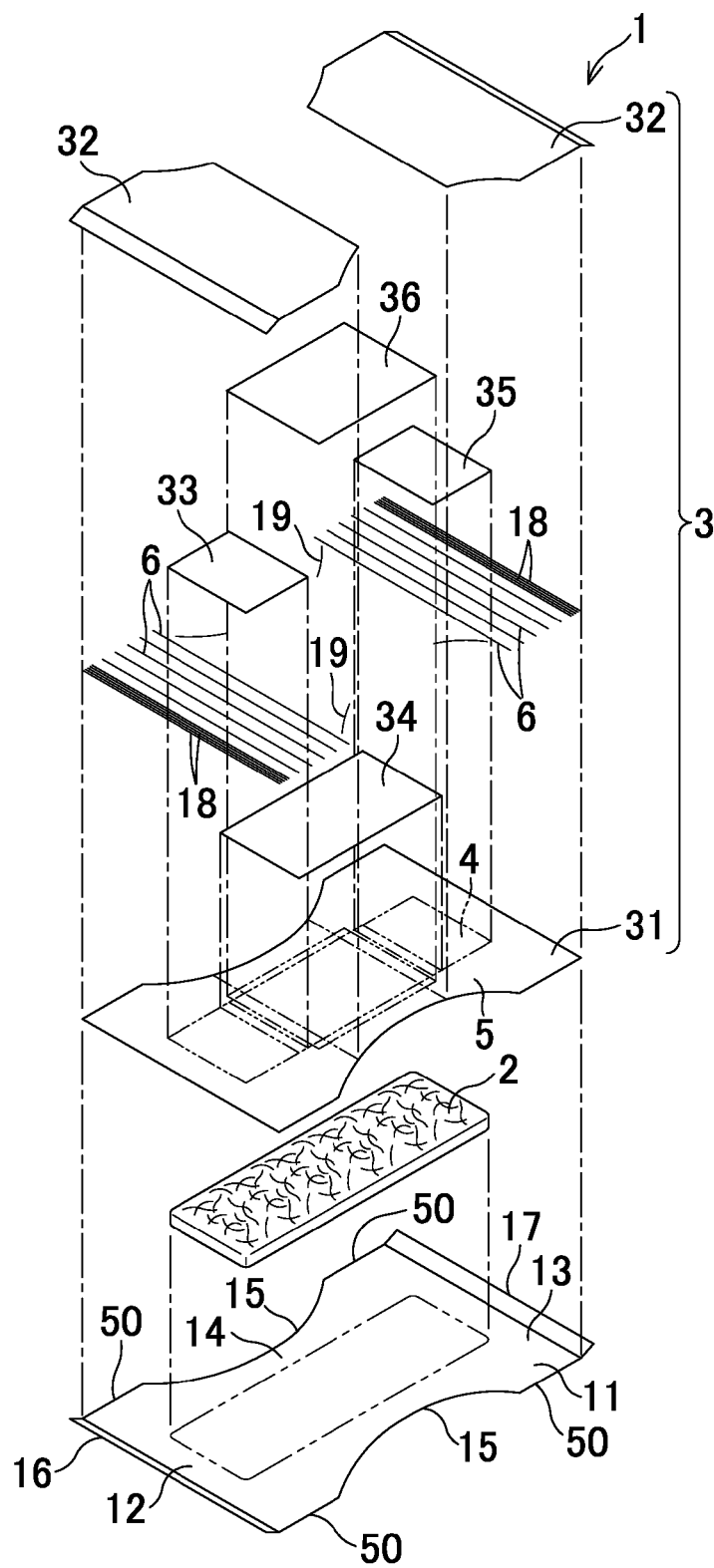
FIG. 1 is an exploded perspective view of a diaper.
Figure 2:
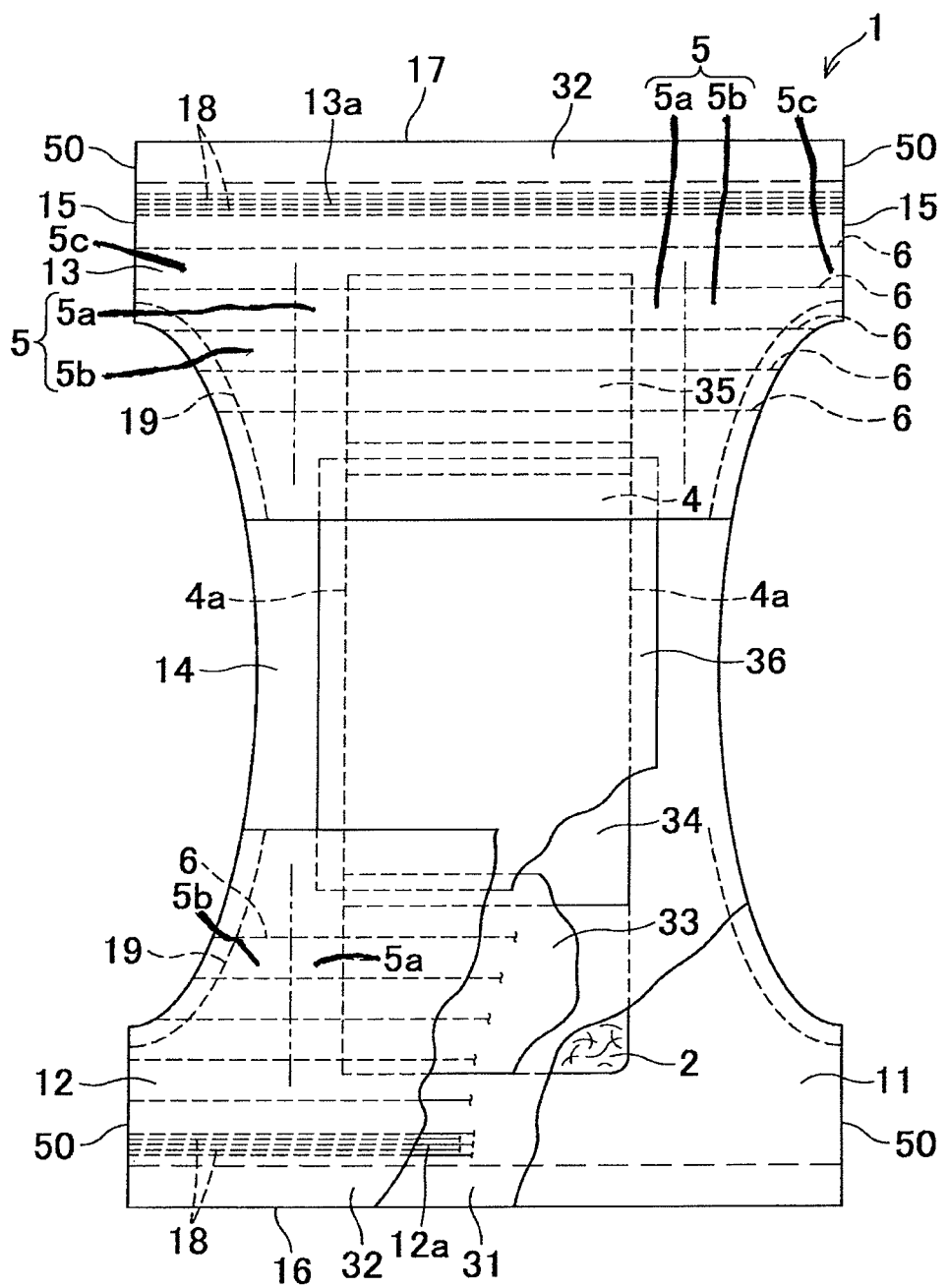
FIG. 2 is a plan view with a partial cutaway of the diaper developed and flattened.

As will be apparent from FIGS. 1 and 2, the diaper 1 comprises a liquid-pervious topsheet 11 facing the wearer's skin, a liquid-impervious chassis 3 which is substantially non-stretchable, and an absorbent structure 2 sandwiched between these elements 3, 11 to absorb bodily fluids. Being flatly developed, the diaper 1 is divided into a front waist region 12, a rear waist region 13 and a crotch region 14 extending between the front and rear waist regions 12, 13. The absorbent structure 2 extends from the crotch region into the front waist region 12 and the rear waist region 13. An area of the chassis 3 is larger than that of the absorbent structure 2 and the chassis is composed of a plurality of sheets, generally, of a liquid-resistant and air-permeable, inner sheet 31 to which the absorbent structure 2 is bonded, and a pair of outer sheets 32 placed upon and bonded to the surface of the inner sheet 31 opposed to the surface thereof to which the absorbent structure 2 is bonded. These two sheets 32 are located in the front waist region 12 and the rear waist region 13, respectively.

The chassis 3 further includes liquid-impermeable, breathable front, rear and intermediate barrier sheets 33, 35, 34 interposed between the inner sheet 31 and front and rear outer sheets 32 and acing the absorbent structure 2 and an intermediate sheet 36 interposed between the outer sheets 32.

The barrier sheets 33, 34, 35 are made of a substantially non-stretchable liquid—impervious, breathable plastic film and combined together so as to become substantially the same as the absorbent structure 2 in shape as well as in size. The connection of these barrier sheets 33, 34, 35 is provided on the surface of the inner sheet 31 opposed to its surface to which the absorbent structure 2 is bonded.

The inner sheet 31, the front and rear outer sheets 32 and the intermediate sheet 36 are substantially non-stretchable and made of an air-permeable, liquid-impervious fibrous nonwoven fabric. An area of the intermediate sheet 36 is larger than that of the intermediate barrier sheet 34 and located together with the barrier sheet 34 in the crotch region 14.

A plurality of first elastic elements 6 are attached under tension between the inner sheet 31 and the outer sheets 32 so as to extend in a cross-body direction (transverse direction) in the front waist region 12 and the outer waist region 13. As shown in FIG. 2, the first elastic elements 6 linearly extend at least partially across an absorbent structure region 4 occupied by the absorbent structure 2 in the cross-body direction and beyond opposite side edges of the absorbent structure 2. An elongation percentage of the first elastic elements 6 attached under tension continuously/gradually increases as the first elastic elements 6 draw away from first side region 5a adjacent to outsides of side edges 4a of the absorbent structure region 4 (or absorbent structure 2) to second side region 5b in the chassis 3. It should be noted that the elongation percentage of the first elastic elements 6 is relatively low in the absorbent structure region 4 and the first side regions 5a and relatively high in the second side regions 5b as entirely compared the elongation percentage in the first and second side regions 5a, 5b.

An outer periphery of the diaper 1, i.e., an outer peripheral of the chassis 3, is contoured by front and rear ends 16, 17 extending in the cross-body direction and opposite side edges 15 extending in the longitudinal direction. In joints 50 extending along the side edges 15 of the front and rear waist regions 12, 13, the inner sheet 31 and the outer sheets 32 are placed upon and bonded to each other while the first elastic elements 6 are intermittently bonded between the inner sheet 31 and the outer sheets 32 in the front and rear waist regions 12, 13 by bonding means such as hot melt adhesives. Thus, the elastic effect of the first elastic elements 6 ensures that the front and rear waist regions 12, 13 come in close contact with the ventral side and the dorsal side of the wearer. In this way, the fit to the wearer's body is improved.

The side edges 15 of the chassis 3 are curved inward with respect to the diaper 1 along middle zones of the side edges 15 and, along the curved segments, third elastic elements 19 to encircle the legs of the wearer are bonded under tension between the inner sheet 11 and the outer sheets 32 by means of bonding means such as adhesives. Front and rear waist bands 12a, 13a extend along the front end 16 and the rear end 17. Along the front and rear waist bands 12a, 13a, the second elastic elements 18 are attached under tension between the inner sheet 31 and the outer sheets 32 by bonding means such as hot melt adhesives.

The diaper 1 is illustrated as an open type one and may be folded back with the topsheet 11 inside so as to place the front end 16 and the rear end 17 upon each other and then the side edges 15 of the front waist region 12 may be placed upon and connected to the side edges 15 of the rear waist region 13 to obtain the diaper 1 ready for wearing. Specifically, the front end 16 and the rear end 17 are left free from each other to form an annular waist-opening (not shown) and the segments of the side edges 15 curved inward form leg-openings (not shown). In the case of the diaper 1 being a pull-on type one (not shown), the side edges 15 of the front and rear waist regions 12, 13 are connected together by bonding means such hot melt adhesives.

More specifically, as mentioned hereinbefore, the first elastic elements 6 are not bonded in the absorbent structure region 4 to the chassis 3 while, in the first and second side regions 5a, 5b, the first elastic elements 6 are bonded between the inner sheet 31 and the outer sheets 32. Such construction in which the first elastic elements 6 are not bonded to the chassis 3 in the absorbent structure region 4 advantageously ensures that the absorbent structure 2 is protected not only against being directly pulled by the first elastic elements 6 but also against undesirable displacement of the absorbent structure 2. Furthermore, it is not apprehended that the absorbent structure 2 might be distorted under a contractile force of the first elastic elements 6. In addition, there is no anxiety that the chassis 3 in the absorbent structure region 4 might get wrinkles under contraction of the first elastic elements and consequentially, it is not apprehended also that the outer appearance of the article might be deteriorated.

Each of the first side regions 5a has a width dependent on the particular type of the absorbent article and, in the case of the diaper 1, each of the first side regions 5a is in the order of 7-15 mm, preferably about 10 mm. If the first side regions 5a are excessively narrow, the regions having a relatively low elongation percentage will be too narrow to achieve the desired effect of the invention and, if the regions having a relatively low elongation percentage are excessively large, on the contrary, a contractile force of the first elastic elements 6 will be insufficient to achieve the desired high fitness. Taking these factors into consideration, the width of the first side regions 5a may be optimized from the particular absorbent article. Furthermore, a dimension spaced apart inward of the absorbent structure region 4 by 3-7 mm may be increased to the foregoing dimension of 7-15 mm.

The second elastic elements 18 and the third elastic elements 19 are also intermittently bonded under tension between the inner sheet 31 and the outer sheets 32 by means of bonding means such as hot melt adhesives.

The second elastic elements 18 intends to tightly hold the diaper fixing around the wearer's waist as well as to prevent bodily wastes leaking therefrom, while the first elastic elements intend to ensure that the diaper 1 is reliably held in close contact with the ventral side as well as with the dorsal side of the wearer with a good fit and thereby to prevent bodily wastes spreading between the diaper 1 and the wearer's skin. Therefore, it is preferable that a tensile stress of each of the second elastic elements 18 is higher than that of the first elastic elements 6.

Accordingly, it is required to establish a relationship that a contractile force of each second elastic element 18 is greater than a contractile force of each first elastic element 6 when the first and second elastic elements 6, 18 are attached to the chassis 3 under tension. This is achieved preferably by setting the respective elongation percentages so as to establish the relationship of the contractile force of each second elastic element 18 is greater than the contractile force of each elastic element 6. Alternatively, the second and first elastic elements 18, 6 may be arranged in such a manner that the contractible forces of each second elastic element 18 and each first elastic element 6 are in a relationship that the former is equal to the latter, and as shown in FIG. 2, respective intervals of the second elastic elements 18 and the first elastic elements 6 in the longitudinal direction orthogonal to the cross-body direction of the diaper 1 are in a relationship that the former is smaller than the latter. The above-described relationship may sometimes invert into that the contractile force of the first elastic elements 6 is greater than the contractile force of the second elastic elements 18 in the case where the elongation percentage of the first elastic elements 6 gradually increases as the first elastic elements 6 draw away from the first side regions 5a toward the side edges 15 of the chassis 3. In such case, the elongation percentage of the first elastic elements 6 spaced apart from the first side regions 5a to vicinity regions 5c of the side edges 15 of the chassis 3 in the second side regions 5b may be set substantially to a constant level to maintain the relationship that the contractile force of the second elastic elements 18 is greater than the contractile force of the elastic elements 6.

In the case of the diaper 1 being of pull-on type in which the front and rear waist regions 12, 13 are connected to each other along the side edges 15, in the side edges 15 or in the joints 50 defined by the side edges 15 in which the first elastic elements 6 are permanently bonded, the first elastic elements 6 are unable to express it elasticity. Specifically, the segment of the first elastic elements 6 which are present in these zones is not included in the first elastic elements 6 having the elongation percentage continuously changing or maintain constant.

Materials for the first elastic elements 6 may be selected from the group consisting of a plurality of rubber strings made of vulcanized rubber or thermoplastic elastomer, elasticized fibrous nonwoven fabrics and elastic plastic films. The first elastic elements 6 preferably comprise a plurality of rubber strings since the desired fit of the diaper 1 to the wearer's body can be assured over a wide range by attaching these rubber strings to the diaper 1 so as to be spaced one from another in the longitudinal direction. Preferably, a distance between each pair of the adjacent rubber strings is appropriately adjusted since this facilitates adjustment of the fit depending on the particular region of the wearer's body.

Stock materials for the topsheet 11 and the inner sheet 31 and the outer sheets 32 may be selected, depending on various aspects, for example, whether the liquid-permeability is required or not and whether the air-permeability is required or not, from the group including fibrous nonwoven fabrics and films both made of thermoplastic resin and a mixture thereof which have been widely used in this field of technique. The topsheet 11 as well as the outer sheets 32 and each of the inner sheet 31 constituting the chassis 3 may comprise a plurality of sheets rather than a single sheet. Regarding the absorbent structure 2 also, the materials well known in the field of the bodily fluid absorbent structure or the like may be appropriately selected as the materials for the absorbent structure 2. It is also possible to provide the topsheet 11 with the well known elements such as the leak-barrier cuffs.

Now a method for making the absorbent article including the first elastic elements 6 having the elongation percentage continuously changing will be described with reference to FIGS. 3 and 4.

Figure 3:
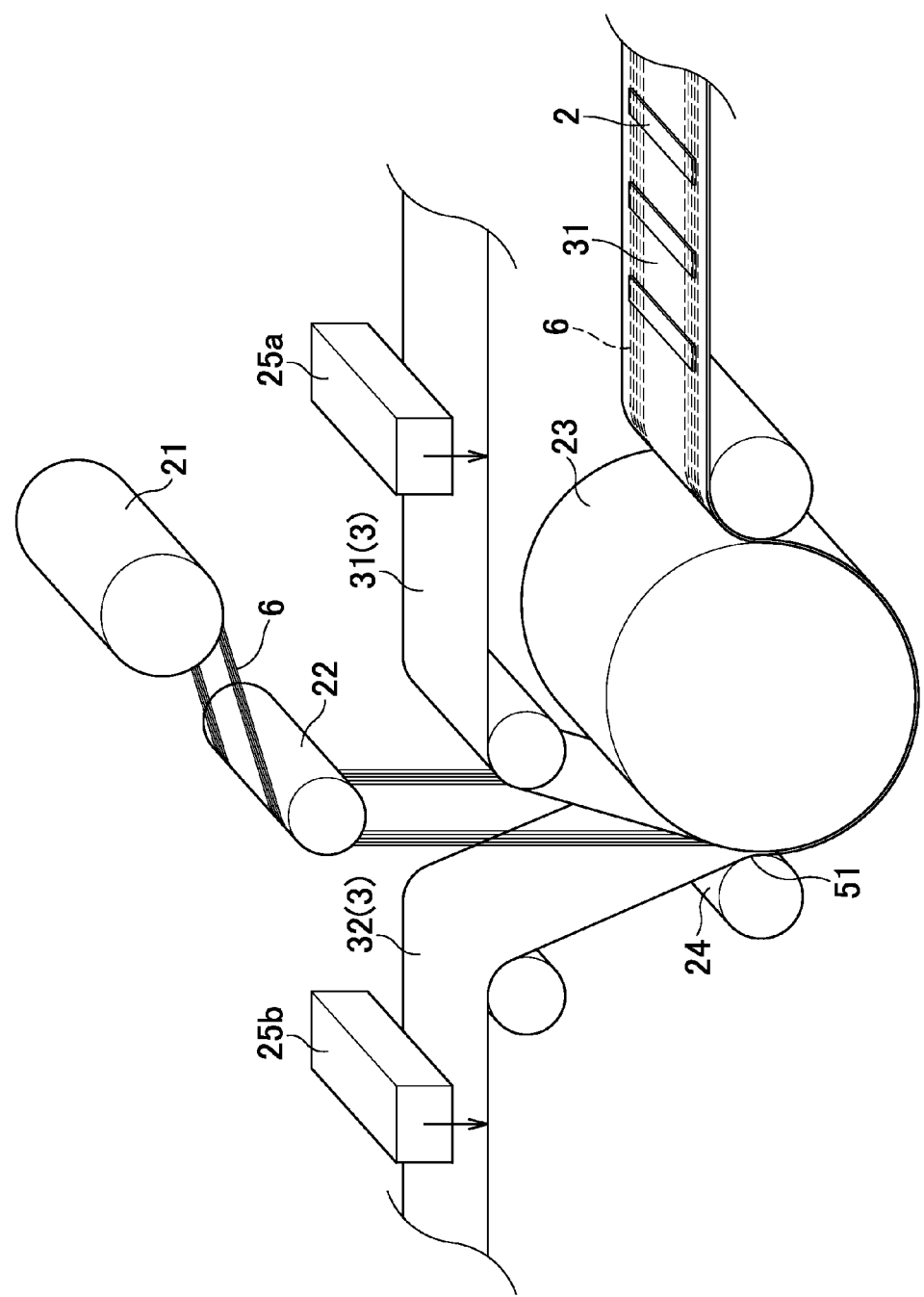
FIG. 3 is a schematic diagram illustrating a method for making the diaper.
Figure 4:
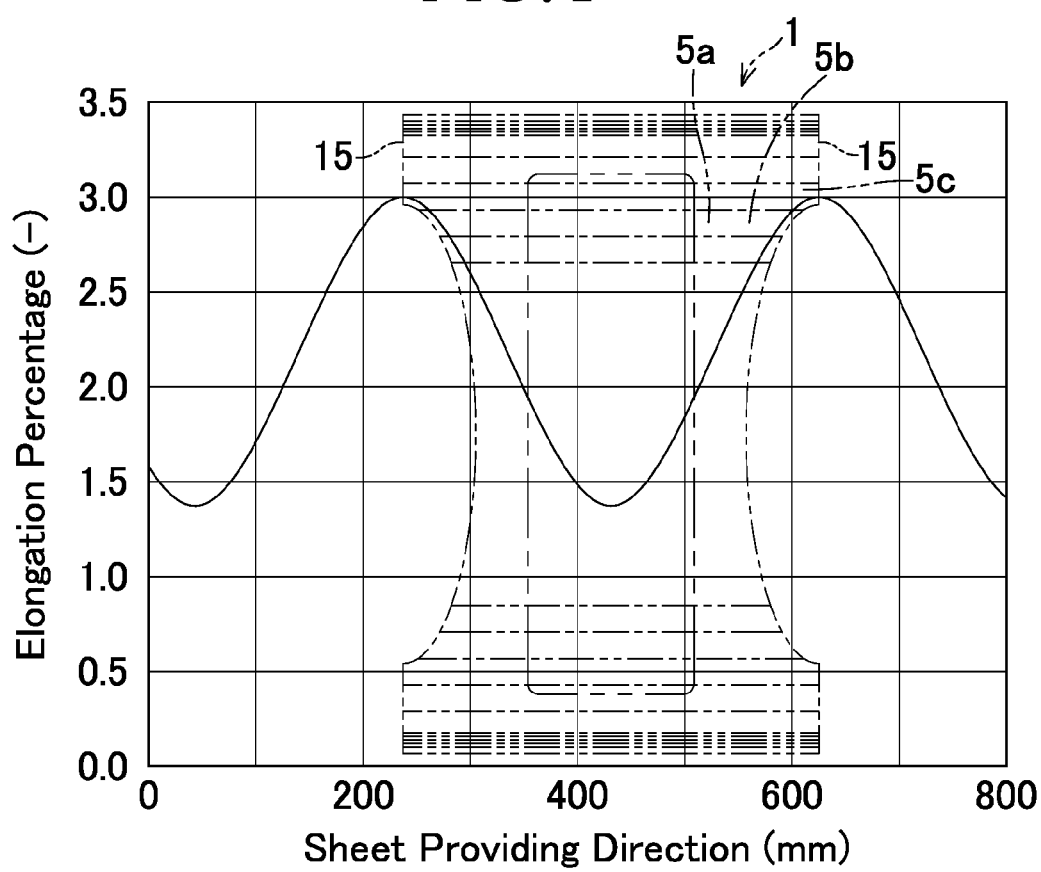
FIG. 4 is a graphic diagram exemplarily showing a pattern in which elongation percentage of a first elastic elements changes.

FIG. 3 is a schematic diagram illustrating the method for making the absorbent article and FIG. 4 is a graphic diagram exemplarily showing a pattern in which the elongation percentage changes of the first elastic elements 6.

Referring to FIG. 3, the method for making the absorbent article on the assumption that the article comprises the absorbent structure 2, the first elastic elements 6 consisting of a plurality of rubber strings and the chassis 3 constituting of the inner sheet 31 and the outer sheets 32.

The inner sheet 31 and the outer sheets 32 are continuously fed at the same constant fed from feed rollers (not shown) via coaters 25a, 25b, respectively, toward a roll gap 51 between a driving roll 23 and a nip roll 24. The first elastic elements 6 are continuously fed from a feed roller 21 via an elongation percentage adjusting roll 22 in the same direction as the inner sheet 31 and the outer sheets 32, i.e., toward the roll gap 51 defined between the driving roll 23 and the nip roll 24 so as to be sandwiched between the inner sheet 31 and the outer sheets 32.

Respective surfaces of the inner sheet 31 and the outer sheets 32 to face each other at the roll gap 51 between the driving roll 23 and the nip roll 24 are coated on paths adapted to have the first elastic elements 6 running thereon with hot melt adhesives by means of the coaters 25a, 25b. The inner sheet 31 and the outer sheets 32 are squeezed together with the first elastic elements 6 between the driving roll 23 and the nip roll 24 so that the assembly comprising the first elastic elements 6 sandwiched and bonded between the inner sheet 31 and the outer sheets 32 is delivered from the driving roll 23. Then the absorbent structure 2 assembled in another step are fed from feed means (not shown) and bonded to the inner sheet 31. In this way, the absorbent article is finally obtained, in which the first elastic elements 6 linearly extends in the transverse direction across the absorbent structure region 4.

The first elastic elements 6 are fed from the feed roller 21 at a constant feed rate and then the feed rate at which the first elastic elements 6 are fed to the chassis 3 is controlled by the elongation percentage adjusting roll 22 so as to be periodically changed according to a predetermined rule. To control the feed rate of the first elastic elements by the elongation percentage adjusting roll 22, a rotation speed of the elongation percentage adjusting roll 22 may be periodically changed according to a predetermined rule by use of the well known rotation speed control means such as a servomotor or VVVF.

With this method of control, the rate at which the first elastic elements 6 are fed to the chassis 3 is enhanced and the elongation percentage of the first elastic elements 6 bonded to the chassis 3 decreases as the rotation speed of the elongation percentage adjusting roll 22 increases. On the contrary, the elongation percentage of the first elastic elements 6 increases as the rotation speed of the elongation percentage adjusting roll 22 decreases. In this manner, the elongation percentage of the first elastic elements 6 can be periodically and continuously changed with respect to the position along the direction in which the chassis 3 is fed, for example, in the pattern as exemplarily illustrated by FIG. 4. Alternatively, the rate at which the first elastic elements 6 are fed from the feed roll 21 may be periodically changed and thereby the elongation percentage of the first elastic elements 6 may be continuously changed.

In the case of the elongation percentage changing pattern exemplarily illustrated by FIG. 4, the elongation percentage of the first elastic elements 6 bonded to the chassis 3 periodically changes in a range of about 1.3 to 3.0. With respect to the diaper 1 indicated by imaginary lines in a graphic diagram of FIG. 4, the absorbent structure 2 and the first side regions 5a may be located in a zone of a relatively low elongation percentage (elongation percentages centering on about 1.3) falling within the range in which the elongation percentage periodically changes while the side edges 15 of the chassis 3 illustrated by the imaginary lines may be located in a zone having the highest elongation percentage (elongation percentage of about 3.0) to obtain the diaper 1 in which the elongation percentage of the first elastic elements 6 continuously increases as the distance from the respective first side regions 5a.

The pattern in which the feed rate of the first elastic elements 6 is periodically changed according to a predetermined rule may be a pattern in which the elongation percentage of the first elastic elements 6 is symmetric about each region having a relatively low elongation percentage, for example, in the form of a sinusoidal wave having each crest flatly deformed or a rotundate trapezoid wave. When the pattern of periodical change is formed of the sinusoidal wave, the elongation percentage of the first elastic elements 6 in the diaper 1 will continuously and monotonically increase as the first elastic elements 6 draws away from the first side regions 5a.

In the diaper 1, each of the first side regions 5a preferably has a width in the order of about 10 mm and, in the regions extending further laterally outward from the respective first side regions 5a, the elongation percentage is preferably adjusted to a relatively high constant level depending on circumstances. Selective dimensioning of the first side regions 5a and adjustment of the elongation percentage in the regions extending laterally outward from the respective first side regions 5a to the relatively high constant level may be achieved, for example, when the feed rate of the first elastic elements 6 is periodically changed in the rotundate trapezoid wave pattern, by selectively adjusting a length (time) of each horizontal segment of the trapezoid wave.

While FIG. 4 illustrates the case in which the elongation percentage of the first elastic elements 6 periodically changes in a range of about 1.3 to 3.0, the elongation percentage of the first elastic elements 6 is not specified and may be appropriately selected depending on a contractile force required to improve a fit of the absorbent article. Depending on the contractile force for the improved fitness, a type of the first elastic elements 6 and a manner in which the first elastic elements 6 are bonded under tension to the chassis 3 may be appropriately selected. For example, in the case of the absorbent article implemented in the form of the diaper 1, the elongation percentage of the first elastic elements 6 in the absorbent structure region 4 and in the first side regions 5a may be set to a range of 1.0 to 2.0 while the elongation percentage of the first elastic elements 6 in the vicinity of the side edges 15 of the chassis 3 may be set to a range of 2.5 to 3.5.

The inner sheet 31 and the outer sheets 32 are coated by the coaters 25a, 25b, respectively, with hot melt adhesive in continuous and/or intermittent fashion. Preferably, these sheets 31, 32 are intermittently coated with hot melt adhesive, for example, in a spiral pattern or in a dotted pattern to avoid interference with stretching and contraction of the first elastic elements 6. Intermittent coating of the hot melt adhesive results in that the elongation percentage of the first elastic elements 6 changes in multistage fashion. Consequentially, a length of each stage in which the elongation percentage of the first elastic elements 6 is uniform can be controlled by selecting interval at which hot melt adhesive is coated. In the case of the absorbent article implemented in the form of the diaper 1, the interval for coating of hot melt adhesive is usually in a range of 2 to 10 mm but this interval may be larger than such range.

While it is theoretically possible to achieve multistage change of the contractile force in the regions of the diaper 1 adapted to be kept in close contact with the ventral side and the dorsal side of the diaper wearer by using a plurality of elastic sheets respectively having different contractile forces, such method will necessarily complicating the production equipment and will be obviously impractical. It is also conceivable to bond the first elastic elements 6 and the chassis 3 to each other as these elements 6 and 3 are stepwise moved in order to multistage change the contractile force of the first elastic elements 6. However, such method will significantly decrease the production rate. In contrast with these methods, the method according to the invention provides for continuous production of the absorbent article in which the elongation percentage of the first elastic elements 6 continuously changes without decreasing the production rate and complicating the production equipment.

In the absorbent structure region 4 of the chassis 3 and occupied by the absorbent structure 2, the first elastic elements 6 may not be bonded to the chassis 3. Such manner of implementation can advantageously avoid undesirable displacement of the absorbent structure 2 since there is no apprehension that the absorbent structure 2 might be directly pulled by the first elastic elements. In addition, there is no anxiety that the absorbent structure 2 might be distorted under the contractile force of the first elastic elements 6. Furthermore, there is no possibility that the absorbent structure region 4 get wrinkles and deteriorate the outer appearance of the article even under contraction of the first elastic elements 6.

While the first elastic elements 6 alone are fed so as to be sandwiched between the inner sheet 31 and the outer sheets 32 so far as FIG. 3 is concerned, it is possible to feed the first elastic elements 6 together with the second elastic elements 18. In this case, the second elastic elements 18 may be fed as the elongation percentage thereof is periodically changed according to a predetermined rule or may be fed as the elongation percentage thereof is maintained constant. It is also possible to divide the inner sheet 31 and/or the outer sheets 32 into a plurality of sections. Furthermore, it is possible to feed the inner sheet 31 and the outer sheets 32 together with the other sheets.

Elongation percentage distribution of the first elastic elements 6 in the absorbent article made by the method according to the invention was evaluated and the result thereof is illustrated in FIG. 5. To evaluate the elongation percentage, the first elastic elements 6 were bonded to the chassis 3, a test piece having a length of about 800 mm as measured in the feed direction for the chassis 3 was cut off from the chassis 3, marks were put on the first elastic elements 6 at the intervals of 30 mm, then hot melt adhesive was dissolved in toluene to separate the first elastic elements 6 and to leave it contract, and a distance D (mm) between each pair of the adjacent marks after contraction was measured. The elongation percentage was calculated as 30/D. It should be understood that "measurement position" in FIG. 5 corresponds to a midpoint of 30 mm, i.e., the distance between each pair of the adjacent marks put on the test piece. Location of the chassis 3 destined to become the diaper 1 is indicated by imaginary lines.

Now a functionality provided by the present invention will be described in reference with FIGS. 6A-6E. FIGS. 6A-6E are schematic diagrams illustrating the manner in which the chassis 3 and the first elastic elements 6 attached thereto are stretched and contracted wherein the elongation percentage of the first elastic elements continuously increases as the distance from the first side regions 5a increases. It is assumed in FIGS. 6A-6E that the elongation percentage increases approximately in four stages from the left side to the right side as viewed in this diagram. It should be understood that the length L of the chassis 3 is constant in the respective stretching stages. While the chassis 3 and the first elastic elements are illustrated as they are separated from each other, the chassis 3 and the first elastic elements 6 are really continuous to each other. It should be understood also that FIGS. 6A-6E illustrates the transversely opposite regions 5 at one side thereof alone.

FIG. 6A illustrates a state in which the first elastic elements 6 have intermittently attached under tension to the chassis 3 by the previously described method, FIG. 6B illustrates a state in which the absorbent article was cut off from the chassis 3 and consequently the first elastic elements 6 were left to contract, and FIGS. 6C and D illustrate respective states in which the first elastic elements 6 are gradually stretched from the state of FIG. 6B in response to the movement of the wearer. In FIGS. 6A-6D, the state in which the first elastic elements 6 are contracted is illustrated by slashes extending downward left and the state in which the first elastic elements 6 are extended is illustrated by slashes extending downward right.

In FIG. 6A, the first elastic element segments 6 (1) through 6 (4) respectively having lengths of x1≧x2≧x3≧x4 before stretching were stretched to the length L of inner sheet 31 of the chassis 3 and the elongation percentage increased in four stages as the first elastic element segments 6 (1) through 6 (4) extend outwardly from the absorbent structure 2. The first elastic elements 6 are herein also intermittently bonded to the outer sheets 32 and inner sheets 31 of the chassis 3.

In FIG. 6B, the first elastic element segments 6 (1) through 6 (4) contract as the first elastic segments 6 (1) through 6 (4) are relieved from the force tending to stretch these segments 6 (1) through 6 (4) in FIG. 6A. FIGS. 6A-6E reflect the assumption that the segments 6 (1) through 6 (4) respectively contract to the lengths x1 through x4, respectively, before being stretched. Upon contraction of the segments 6 (1) through 6 (4), the inner sheet 31 of the chassis 3 becomes pleated and shortened to the same lengths x1 through x4 as those of the segments 6 (1) through 6 (4) as illustrated by FIG. 6B, since the inner sheet 31 of the chassis 3 is non-stretchable and the segments 6 (1) through 6 (4) are intermittently bonded to the inner sheet 31 and outer sheet 32 of the chassis 3. Each of the segments 6 (1) through 6 (4) has an elongation percentage that increases as the distance away from the first side regions 5a increases. Consequentially, a variation in the apparent length of the chassis 3 also increases as a distance from the first side regions 5a increases.

In the state illustrated in FIG. 6C, the first elastic elements 6 are wholly stretched in the first side region 5a as the force tending to stretch the first elastic elements 6 is exerted on the first side region 5a because segment 6 (1) extending in the first side regions 5a is stretchable up to an upper limit corresponding to the length L of the inner sheet 31 of the chassis 3 since the chassis 3 is non-stretchable. In this manner, the segment 6 (1) extending in the first side regions 5a shown in FIG. 6B is slightly stretchable to the upper limits shown in FIG. 6C, and further stretchability is limited to the segments 6 (2) through 6 (4). When additional force tending to stretch the segments 6 (2) through 6 (4) is exerted on the first elastic elements 6 as illustrated in FIG. 6D and E, the segments 6 (2), 6 (3) successively become fully extended to length L and further extension is limited to the segment 6 (4) alone (See FIG. 6E).

More specifically, in response to a stretching force exerted on the first elastic elements 6 in the course of wearing the diaper 1, the first elastic element segment extending in the first side regions 5a having a relatively low elongation percentage are first stretched so as to be slightly displaced up to the upper limit of the stretchable length and then the remaining segments are successively stretched to be displaced by a range expanded as the distance laterally outward from the first side regions 5a increases. In this course, the first side regions 5a get rid of wrinkles, if any, as the first elastic element segment extending in these first side regions 5a reaches the upper limit of stretchability. The absorbent structure region 4 of the chassis 3 becomes wrinkle-free as a stretching force is exerted on the first elastic elements 6. At the same time, the first elastic element segments extending laterally outward from the first side regions 5a and having relatively high elongation percentages serve to enforce the absorbent structure 2 in close contact with the ventral side as well as the dorsal side of the wearer's body and thereby to alleviate a displacement of the absorbent structure 2 and bodily fluid leakage from the ventral side as well as from the dorsal side of the wearer's body.

During use of the diaper 1, a force tending to stretch the first elastic elements 6 generated due to the movement of the wearer causes the first side regions 5a to be slightly displaced but causes the remaining segments of the first elastic elements 6 to be displaced more significantly as a distance laterally outward from the first side regions 5a increases. Consequentially, the absorbent structure 2 is substantially not displaced from its initial position even when the wearer's body moves and the regions at a distance laterally outward from the absorbent structure 2 are sufficiently displaced to follow the movement of the wearer's body. In this way, undesirable displacement of the absorbent structure 2 is effectively alleviated.

While this invention has been described on the basis of the particular embodiment, this invention is not limited to this embodiment. For example, the absorbent article according to the present invention is not limited to the diaper 1 but may be implemented in the form of sanitary napkin, pants for incontinent patient or the like. The diaper 1 may be of pull on-type or open-type.

As a means used to bond the first elastic elements 6 to the chassis 3, hot melt adhesives may be replaced by sealing technique such as heat sealing or sonic sealing technique. In this case, the first elastic elements 6 are preferably formed by rubber strings made of thermoplastic elastomer, or elasticized nonwoven fabrics or films made of thermoplastic resin. Use of the thermoplastic material allows the chassis 3 and the first elastic elements 6 to be integrally heat-sealed together and thereby eliminates an anxiety that the first elastic elements 6 might be separated from the chassis 3 at the seal points as the first elastic elements 6 contracts and the elongation percentage might change so as to be uniformized. It should be understood that hot melt adhesives may be used with the sealing technique.

It is also possible to control the elongation percentage of the first elastic elements 6 so that the elongation percentage continuously increases or decreases within a range of percentages higher than in the first side regions 5a as the distance laterally outward from those first side regions 5a increases. Such arrangement facilitates the diaper 1 to be deformed in the regions having relatively high elongation percentages. In view of this, the absorbent article such as the diaper may be configured so that the regions thereof having relatively high elongation percentage may face the regions of the wearer's body apt to move significantly during use of the article and substantially these regions may be displaced to follow the movement of the wearer's body to avoid undesirable displacement of the absorbent structure 2 as perfectly as possible. According to this invention, both the region 4 occupied by the absorbent structure 2 and the first side regions 5a can get rid of wrinkles and this feature is effective to keep the absorbent structure 2 in close contact with the wearer's body.

What is claimed is:

1. An absorbent article, comprising:
    a chassis having a front waist region, a rear waist region, a crotch region, a front waist band associated with said front waist region and a rear waist band associated with said rear waist region and said chassis made of substantially non-stretchable material and being liquid-impermeable in at least said crotch region;
    an absorbent structure extending along a longitudinal direction of the absorbent article from said crotch region into said front and rear waist regions;
    first elastic elements attached to said chassis, extending only in the front and rear waist regions in a cross-body direction of the absorbent article outside of opposite side edges of said absorbent structure and crossing an absorbent structure region occupied by said absorbent structure in the cross-body direction, wherein the cross-body direction is orthogonal to the longitudinal direction; and
    second elastic elements bonded only to the front and rear waist regions and configured to extend along a leg of the wearer in such a manner that the second elastic elements do not extend into the crotch region,
    wherein an elongation percentage of the first elastic elements is lower in said absorbent structure region as well as in first side regions laterally adjacent to and outside at least respective ones of said opposite side edges of said absorbent structure region in the cross-body direction, and is higher in second side regions laterally adjacent to and outside at least respective ones of said first side regions in the cross-body direction, and said elongation percentage gradually increases in the cross-body direction from each first side region toward each second side region.

2. The absorbent article according to claim 1, wherein:
said article further comprises a third elastic element attached along said front and rear waist bands, and
a tensile stress of said first elastic elements is lower than that of said third elastic element.

3. An absorbent article having a front waist region, a rear waist region, and a crotch region extending between the front and rear waist regions, said absorbent article comprising
a liquid-pervious topsheet adapted to face a wearer's skin,
a liquid-impervious chassis which is substantially non-stretchable, and
an absorbent structure between the topsheet and the chassis and extending from the crotch region into the front waist region and the rear waist region,
a plurality of first elastic elements extending only in the front and rear waist regions and attached to the chassis under tension extending in a cross-body direction in the front waist region and the rear waist region and at least partially across an absorbent structure region occupied by the absorbent structure and beyond opposite side edges of the absorbent structure, and
second elastic elements bonded only to the front and rear waist regions and configured to extend along a leg of the wearer in such a manner that the second elastic elements do not extend into the crotch region,
wherein an area of the chassis is larger than that of the absorbent structure,
wherein the chassis comprises
an inner sheet to which the absorbent structure is bonded,
a front outer sheet located in the front waist region,
a rear outer sheet located in the rear waist region, each of said outer sheets placed upon and bonded to a surface of the inner sheet that is opposite a surface of the inner sheet to which the absorbent structure is bonded,
at least one liquid-impermeable, breathable barrier sheet between the inner sheet and outer sheets and facing the absorbent structure, and
an intermediate sheet layered between said outer sheets and said barrier sheets and extending longitudinally between said front and rear outer sheets the outer sheets,
wherein the inner sheet, the front and rear outer sheets and the intermediate sheet are substantially non-stretchable and made of an air-permeable, liquid-impervious fibrous nonwoven fabric,
wherein said plurality of first elastic elements is attached to the chassis between the inner sheet and the outer sheets; and
wherein an elongation percentage of the first elastic elements attached under tension increases as the first elastic elements draw away from a first side region adjacent to outsides of side edges of the absorbent structure region to a second side region in the chassis.

* * * * *